US00PP23380P2

(12) United States Plant Patent
Sobek

(10) Patent No.: US PP23,380 P2
(45) Date of Patent: Feb. 5, 2013

(54) **NEW GUINEA *IMPATIENS* PLANT NAMED 'IMGZ0006'**

(50) Latin Name: *Impatiens hawkeri*
Varietal Denomination: IMGZ0006

(75) Inventor: Renate Sobek, Bad Salzuflen (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/200,839

(22) Filed: Oct. 3, 2011

(51) Int. Cl.
*A01H 5/00* (2006.01)

(52) U.S. Cl. ..... Plt./318.3; Plt./318.1

(58) Field of Classification Search ..... Plt./318.1, Plt./318.3
See application file for complete search history.

*Primary Examiner* — Susan McCormick Ewoldt
(74) *Attorney, Agent, or Firm* — Joshua L. Price

(57) ABSTRACT

A new New Guinea *Impatiens* plant named 'IMGZ0006' particularly distinguished by the has very large, flat flowers of brilliant orange-red color with a large white to very light red central blotch and a distinct red-purple eye, deep green glossy foliage with deep red veining, and a taller plant habit.

1 Drawing Sheet

Latin name of the genus and species of the plant claimed: *Impatiens hawkeri.*

Varietal denomination: 'IMGZ0006'.

BACKGROUND OF THE NEW PLANT

The present invention comprises a new New Guinea *Impatiens*, botanically known as *Impatiens hawkeri*, and hereinafter referred to by the variety name 'IMGZ0006'.

'IMGZ0006' is a product of a planned breeding program. The new cultivar has very large, flat flowers of brilliant orange-red color with a large white to very light red central blotch and a distinct red-purple eye, deep green glossy foliage with deep red veining, and a taller plant habit.

'IMGZ0006' originated from a hybridization made in the June 2005 in a controlled breeding environment in Hillscheid, Germany.

The female parent was the commercial, unpatented variety 'Paradise Amoya' with a more salmon and white color, a smaller size flower and is earlier to flower.

The male parent of 'IMGZ0006' was a proprietary, unpatented plant designated 'K05-5618-1' with light pink flower color, smaller flower size and lighter colored foliage.

The resultant seed was sown in November 2005 in a greenhouse in Moncarapacho, Portugal, and 'IMGZ0006' was selected there as one flowering plant within the progeny of the stated cross in the spring of 2006.

The first act of asexual reproduction of 'IMGZ0006' was accomplished when vegetative cuttings were propagated from the initial selection in June 2006 in a controlled environment in Moncarapacho, Portugal.

BRIEF SUMMARY OF INVENTION

Horticultural examination of plants grown from cuttings of the plant initiated in March 2007 in Hillscheid, Germany and continuing thereafter, has demonstrated that the combination of characteristics as herein disclosed for 'IMGZ0006' are firmly fixed and are retained through successive generations of asexual reproduction.

'IMGZ0006' has not been observed under all possible environmental conditions. The phenotype may vary significantly with variations in environment such as temperature, light intensity and day length.

A Plant Breeder's Right for this cultivar was applied for in Canada on Dec. 24, 2010, #10-7140. 'IMGZ0006' has not been made publicly available more than one year prior to the filing of this application.

The following traits have been repeatedly observed and are determined to be basic characteristics of the new variety. The combination of these characteristics distinguishes this *Impatiens* as a new and distinct variety.

BRIEF DESCRIPTION OF THE PHOTOGRAPHS

The accompanying photographic drawing shows typical flower and foliage characteristics of 'IMGZ0006' with colors being as true as possible with an illustration of this type. The photographic drawing shows a flowering plant of the new variety growing in 4.5 inch pot and a close-up of the flowers.

DETAILED BOTANICAL DESCRIPTION

The aforementioned photographs were taken in the end of March 2011 from plants grown in a greenhouse trial in Gilroy, Calif. USA. These plants were growing in 4.5 inch pots and were approximately 8-9 weeks of age.

The plant descriptions and measurements were taken in mid May 2011 on eleven week old plants growing in a greenhouse in Andijk, The Netherlands. Cuttings were stuck in early February for rooting, planted into 12 cm pots in late February, and were grown, without pinching, on benches in a greenhouse, initially at a temperature of 20° C.

Color references are made to The Royal Horticultural Society Colour Chart (R.H.S.) 2001.

TABLE 1

DIFFERENCES BETWEEN THE NEW VARIETY 'IMGZ0006' AND A SIMILAR VARIETY

| | 'IMGZ0006' | 'ORANGE NEPTIS' (EU Plant Breeders Right Under 'Kinepor' #EU7312) |
|---|---|---|
| Flower color: | More salmon-orange | Deeper orange, more brilliant |
| Flower eye color: | Distinct | Very weak |
| Flower size (width): | 8.3-9.2 cm | 6.8-7.1 cm |
| Foliage color: | Dark green | Medium green |
| Leaf shape: | Narrow | Wider |

Plant:

*Form, growth and habit*.—Initially medium sized, becoming taller during the summer, mounded, with a medium number of branches.

*Plant height*.—17.0 cm.

*Plant height* (*inflorescence included*).—18.0-20.0 cm.

*Plant width*.—27.0-29.0 cm.

Roots:

*Number of days to initiate roots*.—7 days at about 22 degrees C.

*Number of days to produce a rooted cutting*.—15-18 days at 22 degrees C.

*Type*.—Fine, fibrous, free branching.

*Color*.—RHS 159D.

Foliage:

*Arrangement*.—Simple leaves, mainly in whorls.

*Young leaf, color upper surface*.—RHS 137C.

*Young leaf, color lower surface*.—Closest RHS 184A.

*Mature leaf, color upper surface*.—RHS 137B.

*Mature leaf, color lower surface*.—Closest to RHS 184B.

*Length*.—11.0-13.5 cm.

*Width*.—3.3-3.5 cm.

*Shape*.—Elliptical, relatively narrow.

*Base shape*.—Acute.

*Apex shape*.—Acuminate.

*Margin*.—Serrulate, with short bristles.

*Texture*.—Slightly waxy and glossy on the upper surface, glabrous on both surfaces.

*Color of veins, upper surface*.—RHS 53A.

*Color of veins, lower surface*.—RHS 185A.

*Petiole color, upper side*.—RHS 53B.

*Petiole color, lower side*.—RHS 185B.

*Length*.—Approximately 1-2 cm.

*Diameter*.—0.3 cm.

*Texture*.—Glabrous.

Stem:

*Color of stem*.—RHS 185A.

*Length of stem*.—About 9-13 cm.

*Diameter*.—0.6-0.8 cm.

*Length of internodes*.—Approximately 3-5 cm.

*Texture*.—Smooth, glabrous.

*Number of branches*.—9-11.

*Color of peduncle*.—RHS 185A.

*Length of peduncle*.—6.0-6.5 cm.

*Peduncle diameter*.—0.2 cm.

*Texture*.—Glabrous.

Inflorescence:

*Blooming habit*.—Continuous flowering from spring through fall.

*Type of inflorescence*.—Solitary flowers emerge from the upper leaf nodes of the stem.

*Number of flowers per node*.—1-3 open flowers and additional buds in various stages of development.

*Quantity of flowers per plant*.—2-4 open flowers plus 6-10 buds.

*Lastingness of individual blooms on the plant*.—About 6-9 days.

*Fragrance*.—None.

Bud (just before opening):

*Color*.—RHS 43A.

*Length*.—Up to 3.1 cm.

*Width*.—Up to 1.8 cm.

*Shape*.—Ovate.

Immature flowers:

*Color of petals, upper surface*.—RHS 41A.

*Color of petals, lower surface*.—RHS 43C.

Mature flowers:

*Flower, vertical length*.—8.8-9.5 cm.

*Flower, horizontal width*.—8.3-9.2 cm.

*Flower depth*.—1.5-2.0 cm.

*Color of petals, upper surface*.—RHS 33A to RHS 33B; with a large central blotch of mainly RHS N155D and sometimes RHS 49A to RHS 49D; and a basal eye zone of RHS N57B.

*Color of petals, lower surface*.—RHS 41B.

*Petal shape*.—Nearly round to somewhat zygomorphic.

*Petla apex shape*.—Rounded or broadly obcordate.

*Petal margin*.—Entire.

*Petal texture, upper surface*.—Papillose.

*Lower surface*.—Papillose.

Calyx:

*Arrangement*.—One large sepal bearing the spur, 2 small, lateral sepals, and 1 fused keel.

*Large sepal(s) Color, visible/lower surface*.—RHS 50C.

*Length*.—2.6 cm.

*Width*.—1.7 cm.

*Shape*.—Ovate to elliptical.

*Apex shape*.—Acuminate.

*Base*.—Fused.

*Margins*.—Entire.

*Texture, upper surface*.—Papillose.

*Texture, lower surface*.—Papillose.

*Lateral sepals Color of surface*.—RHS 166B.

*Length*.—1.9-2.2 cm.

*Width*.—0.6-0.7 cm.

*Shape*.—Lanceolate.

*Apex shape*.—Acute.

*Base*.—Fused.

*Margins*.—Entire.

*Texture, upper surface*.—Glabrous.

*Lower surface*.—Glabrous.

*Keel color*.—From RHS 46A to more brownish tones, closest to RHS 185A.

*Length of keel*.—About 3.0 cm.

Spur:

*Color*.—RHS 53B mainly, RHS 53A at the tip.

*Length*.—5.2-5.5 cm.

*Diameter*.—0.3 cm at the base, 0.05 cm at tip.

Reproductive organs androecium: 5 stamen, fused with the anthers hooded, and surrounding the young gynoecium.

*Shape*.—Roughly ovoid.

*Length of androeceum*.—0.7 cm.

*Width of androecium*.—0.5 cm.

*Surface color*.—RHS N57B, fading towards margin.

*Pollen amount*.—Plenty.

*Color of pollen*.—RHS 8D.

Gynoecium:

*Pistil*.—One, elongate.

*Pistil length*.—0.6 cm.

*Style and stigma, total length*.—0.2 cm.

*Style color*.—RHS 53C.

*Stigma color*.—RHS 53C.

*Ovary color*.—RHS 183A.

*Fertility/seed set*.—Has not been observed on this hybrid.

*Disease/pest resistance*.—Has not been observed on this hybrid.

What is claimed is:

1. A new and distinct variety of New Guinea *Impatiens* plant named 'IMGZ0006' substantially as illustrated and described herein.

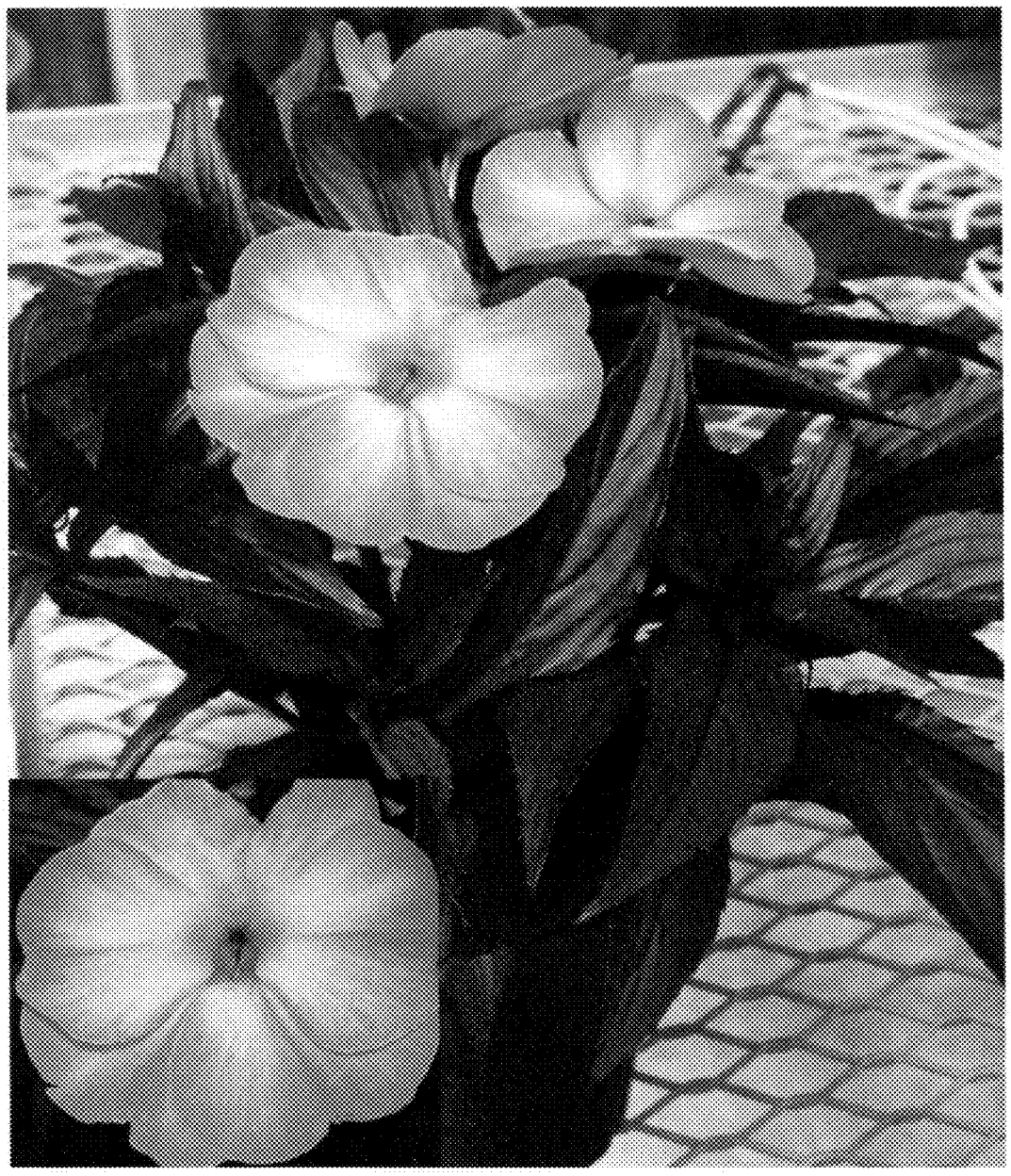

* * * * *